United States Patent
Ouchi

(10) Patent No.: US 6,409,678 B1
(45) Date of Patent: Jun. 25, 2002

(54) ENDOSCOPIC BIOPSY FORCEPS

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/519,854

(22) Filed: Mar. 6, 2000

(30) Foreign Application Priority Data

Apr. 14, 1999 (JP) ............................................ 11-106570

(51) Int. Cl.$^7$ ................................................ A61B 10/00
(52) U.S. Cl. ...................................... 600/562; 606/205
(58) Field of Search ................................ 600/564, 565, 600/567; 606/205, 206, 207, 208, 209

(56) References Cited

U.S. PATENT DOCUMENTS

| 4,178,810 A | 12/1979 | Takahashi |
| 5,820,546 A | 10/1998 | Ouchi |
| 5,899,850 A | 5/1999 | Ouchi |
| 5,931,810 A | * 8/1999 | Grabek ........................ 604/51 |
| 6,099,550 A | * 8/2000 | Yoon ........................... 606/205 |

FOREIGN PATENT DOCUMENTS

| EP | 491890 | 2/0000 |
| JP | 53-26876 | 7/1978 |
| JP | 63-64212 | 12/1988 |
| JP | 26-08675 | 2/1997 |

* cited by examiner

Primary Examiner—John P. Lacyk
Assistant Examiner—Pamela Wingood
(74) Attorney, Agent, or Firm—Greenblum & Bernstein P.L.C.

(57) ABSTRACT

Endoscopic biopsy forceps that allows a non-deformed, high-quality tissue specimen to be readily collected from the correct target position. Needles that extend forward to project into a pair of forceps cups are offset from the center of said pair of forceps cups.

14 Claims, 6 Drawing Sheets

ENDOSCOPIC BIOPSY FORCEPS

BACKGROUND OF THE INVENTION

The present invention relates to endoscopic biopsy forceps that is passed through the forceps channel in an endoscope to collect a tissue specimen for biopsy from within a body cavity.

Endoscopic biopsy forceps generally comprise a sheath to be inserted into or removed from the forceps channel in an endoscope, a manipulating wire extending through the sheath, and a pair of forceps cups provided at the distal end of the sheath that are driven to open and close by advancing and retracting the manipulating wire along the longitudinal axis.

To collect a tissue specimen, the forceps cups are closed but they might slip on the mucosal surface and fail to attain the intended result. To avoid this problem, some endoscopic biopsy forceps are provided with a needle that extends forward to project into the central part of a pair of forceps cups.

To collect a tissue specimen for biopsy with this type of endoscopic forceps, a pair of forceps cups are opened and the needle is pierced through the mucous membrane in the diseased part so as to fix the forceps cups in position; then, the manipulating wire is pulled toward the operator to close the forceps cups, whereupon a tissue specimen is collected within the pair of forceps cups.

A problem with this approach is that the needle pierced into the central part of the specimen can damage and deform the tissue of this vital part of the specimen to such an extent that the operator is unable to determine correctly if the diseased part is malignant or not.

SUMMARY OF THE INVENTION

An object, therefore, of the invention is to provide endoscopic biopsy forceps that allows a non-deformed, high-quality tissue specimen to be readily collected from the correct target position.

According to the invention, a needle or needles are provided that extend forward to project into and/or along a pair of forceps cups and this allows the tip portion of biopsy forceps to be positively secured on the mucosal membrane so that a tissue specimen of the diseased part can be easily detached from the correct target position and collected into the forceps cups. What is more, the needle or needles are offset from the center of the pair of forceps cups and this enables collection of a non-deformed, high-quality tissue specimen.

Endoscopic biopsy forceps preferably comprises a sheath, a manipulating wire extending through the sheath, a pair of forceps cups provided at the distal end of said sheath which are driven to open and close like beaks by advancing and retracting the manipulating wire along the longitudinal axis, and a needle that extends forward to project into and/or along said one pair of forceps cups, the needle being offset from the center of said one pair of forceps cups.

If desired, a plurality of needles may be positioned side by side and offset from the center of said one pair of forceps cups.

The present disclosure relates to the subject matter contained in Japanese patent application No. Hei. 11-106570 (filed on Apr. 14, 1999), which is expressly incorporated herein by reference in its entirety.

DESCRIPTION OF THE PREFERRED EMBODIMENT

Embodiments of the invention are described below with reference to the accompanying drawings.

Figure 3:
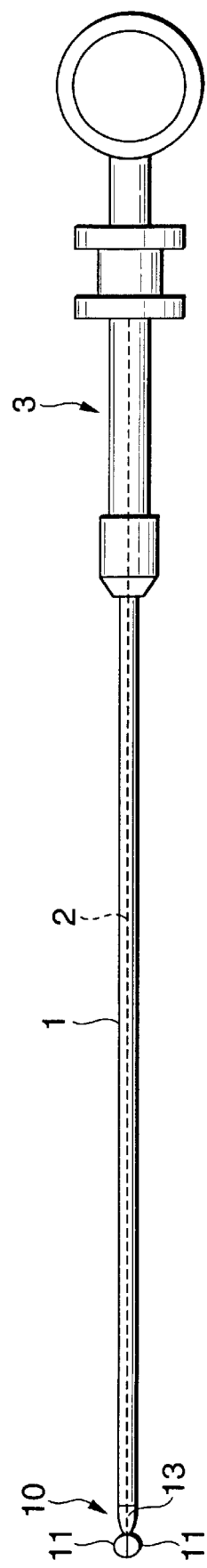
FIG. 3 is a side view showing the general construction of the endoscopic biopsy forceps according to the first embodiment of the invention.

FIG. 3 shows endoscopic biopsy forceps according to a first embodiment of the invention. The forceps comprises a flexible sheath 1 to be inserted into or removed from the forceps channel in an endoscope (not shown) and a manipulating wire 2 that extends through the entire length of the flexible sheath 1 and which is free to advance and retract along the longitudinal axis.

A manipulating section 3 for controlling the manipulating wire 2 to either advance or retract is coupled to the basal end of the sheath 1 (which is the closer to the operator). An actuating tip 10 that can be driven with the manipulating wire 2 is coupled to the distal end of the sheath 1.

Figure 1:
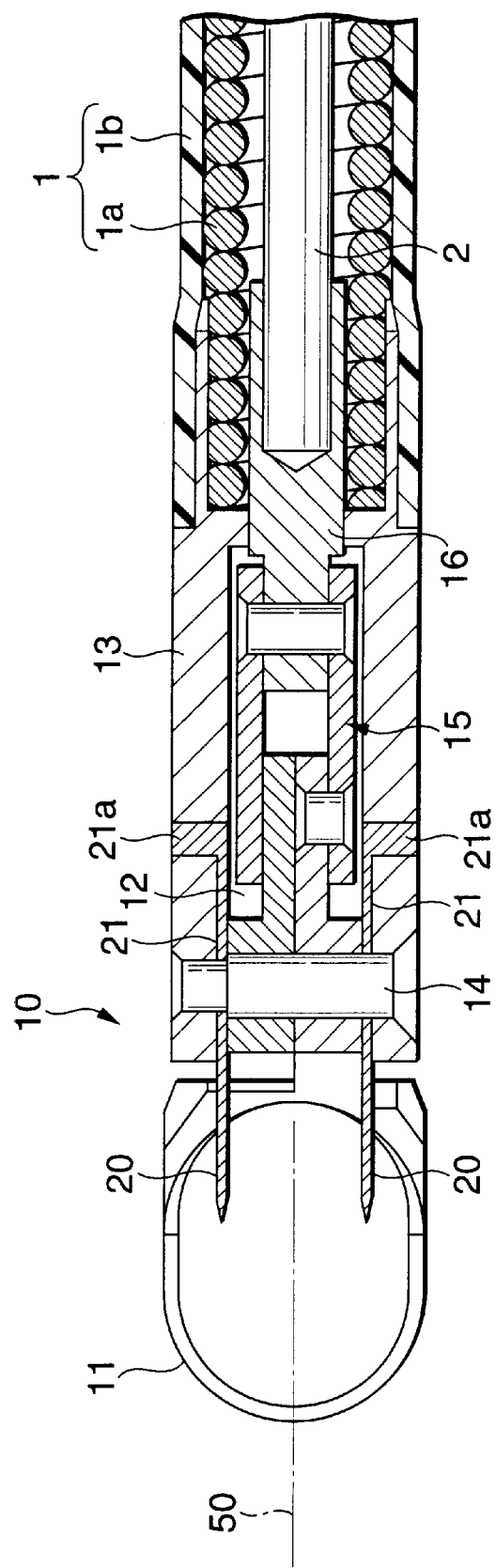
FIG. 1 is a plan view showing in section the tip portion of endoscopic biopsy forceps according to a first embodiment of the invention.
Figure 2:
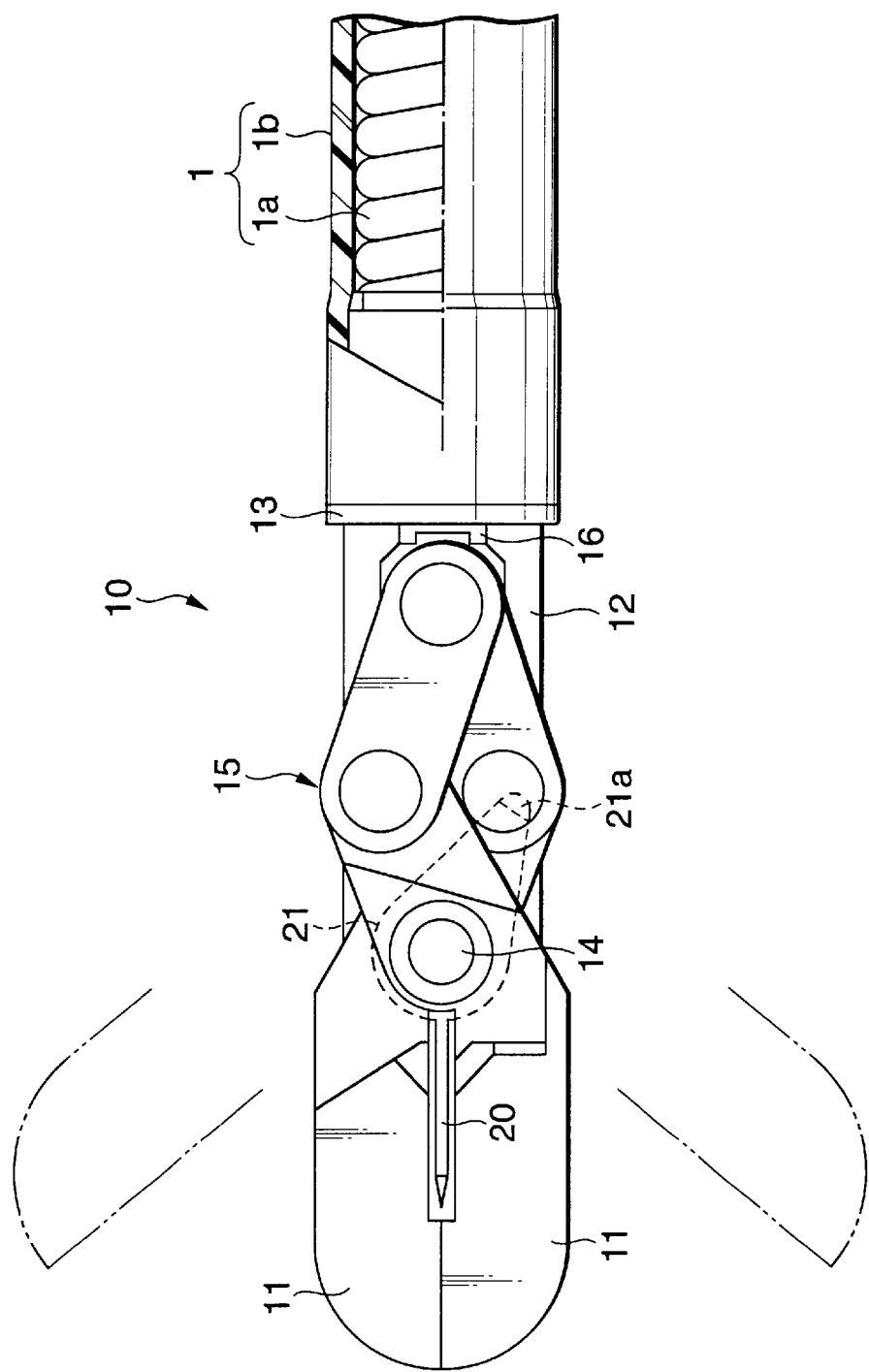
FIG. 2 is a side view showing, with part taken away, the tip portion of the endoscopic biopsy forceps according to the first embodiment of the invention.

FIGS. 1 and 2 show the actuating tip 10 in enlarged form. FIG. 2 is a side view with part taken away, and FIG. 1 is a plan view in partial section. The sheath 1 consists of a coil pipe 1a covered with a flexible tube 1b; the coil pipe 1a may be formed of a fine stainless steel wire that is wound in close turns in a specified diameter. If desired, either the coil pipe 1a or the flexible tube 1b may be omitted.

Coupled securely to the tip of the sheath 1 is a tip assembly 13 having a large slit 12 formed in the front portion. A support shaft 14 is mounted in the tip assembly 13 in such a way that it crosses the neighborhood of the distal end of the slit 12.

A pair of forceps cups 11 are supported rotatably on the shaft 14 so that they can open and close like beaks by rotating about the shaft 14. A known link mechanism 15 is provided within the slit 12 such that it is driven by the manipulating wire 2 to open and close the forceps cups 11.

The link mechanism 15 is a pantograph consisting of four links joined pivotally in parallelogram form and the two front links are an integral part of the pair of forceps cups 11 so that they pivot on the support shaft 14.

A driving rod 16 is coupled to the rear end of the link mechanism 15. The distal end of the manipulating wire 2 is securely coupled to the driving rod 16 so that the link mechanism 15 can be actuated by remote control from the basal end of the sheath 1. If the manipulating wire 2 is pushed forward, the pair of forceps cups 11 open as indicated by one-long-and-two-short dashed lines in FIG. 2; if the manipulating wire 2 is pulled toward the operator, the cups close as indicated by solid lines.

Two needles 20 extend forward from the distal end of the tip assembly 13 so that they project into the pair of forceps cups 11. Each of the needles 20 is an integral projecting part of a mount seat 21 in thin plate form; the support shaft 14 is passed through the holes in the mount seats 21 so that they are in engagement with the tip assembly 13.

A securing projection 21a erected at the rear end of each mount seat 21 is fitted into a hole made in each side wall of the tip assembly 13; as a result, the mount seats 21 are secured in position so that they will not rotate about the support shaft 14.

As FIG. 2 shows, the two needles 20 lie in the same plane as the surface of engagement between the two forceps cups 11. It should, however, be noted that both needles are offset from the longitudinal axis 50 through the center of the forceps cups 11 so that they are symmetrical with respect to said longitudinal axis.

To collect a tissue specimen for biopsy using the endoscopic biopsy forceps according to the first embodiment of the invention, the following procedure may be taken. First, the sheath 1 is passed through the treatment tool insertion channel in an endoscope (not shown) so that the actuating tip 10 is guided into a body cavity. A pair of forceps cups 11 are opened, the needles 20 are pierced through the mucous membrane of the diseased part so that the actuating tip 10 is fixed in position, and subsequently the manipulating wire 2 is pulled toward the operator to close the pair of forceps cups 11.

The needles 20 pierced through the mucous membrane of the diseased part allow the actuating tip 10 to be positively secured on the mucosal surface so that a specimen of the diseased part can be easily detached from the right position and collected into the forceps cups 11.

Since the needles 20 are not pierced in the central part of the tissue specimen but in positions offset from the center, the collected specimen is not deformed and by microscopic examination of it, the doctor can determine correctly if the diseased part is malignant or not.

The present invention is by no means limited to the foregoing embodiment and it may be applied to other techniques of biopsy, for example, "hot biopsy" in which a specimen for biopsy is collected with a radio-frequency current being applied to the forceps cups 11 via the manipulating wire 2.

Figure 4:
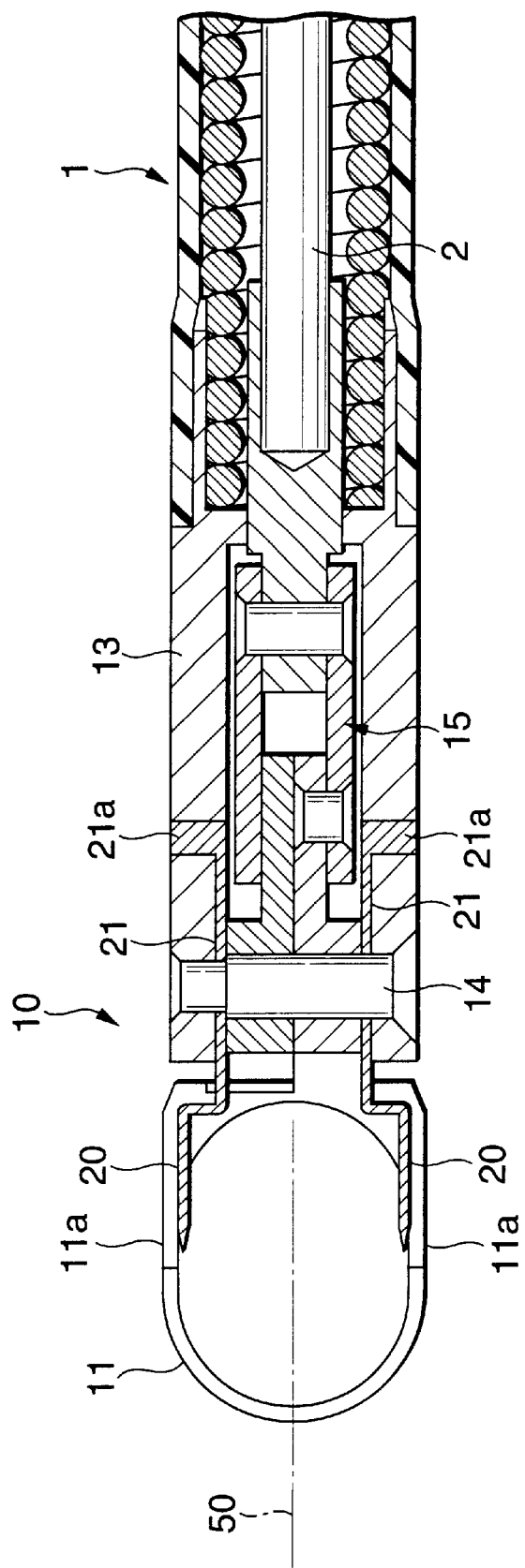
FIG. 4 is a plan view showing in section the tip portion of endoscopic biopsy forceps according to a second embodiment of the invention.
Figure 5:
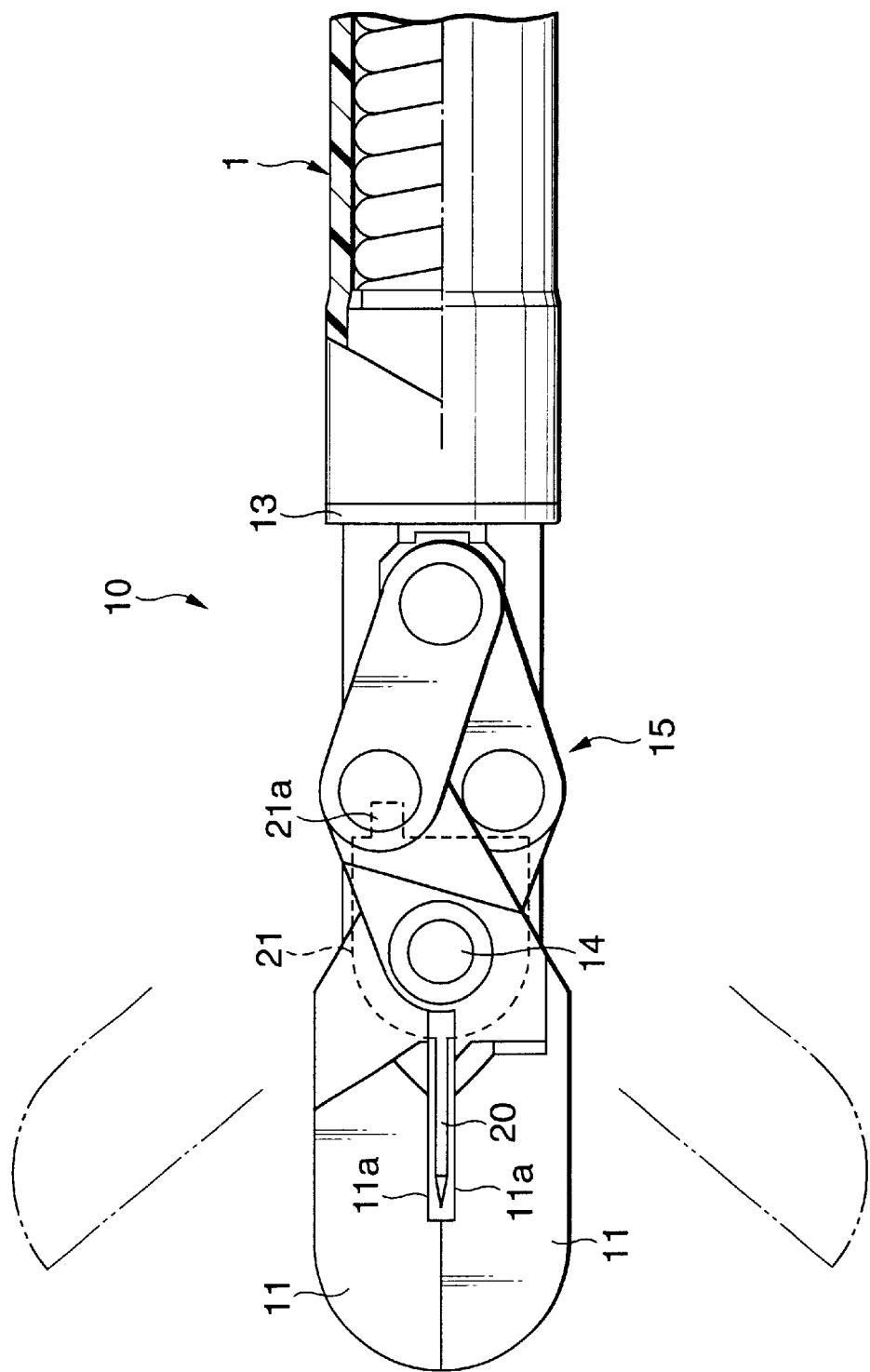
FIG. 5 is a side view showing, with part taken away, the tip portion of the endoscopic biopsy forceps according to the second embodiment of the invention.

In the first embodiment, the needles 20 project into the forceps cups 11 but this is not the sole case of the invention. As shown in FIGS. 4 and 5 which show endoscopic biopsy forceps according to a second embodiment of the invention, the needles 20 may project along the peripheries of the forceps cups 11.

In this case, relief grooves 1a must be formed in the forceps cups 11 to avoid interference with the needles 20. Also note that the mount seats 21 in the second embodiment are formed to be larger than in the first embodiment.

Figure 6:
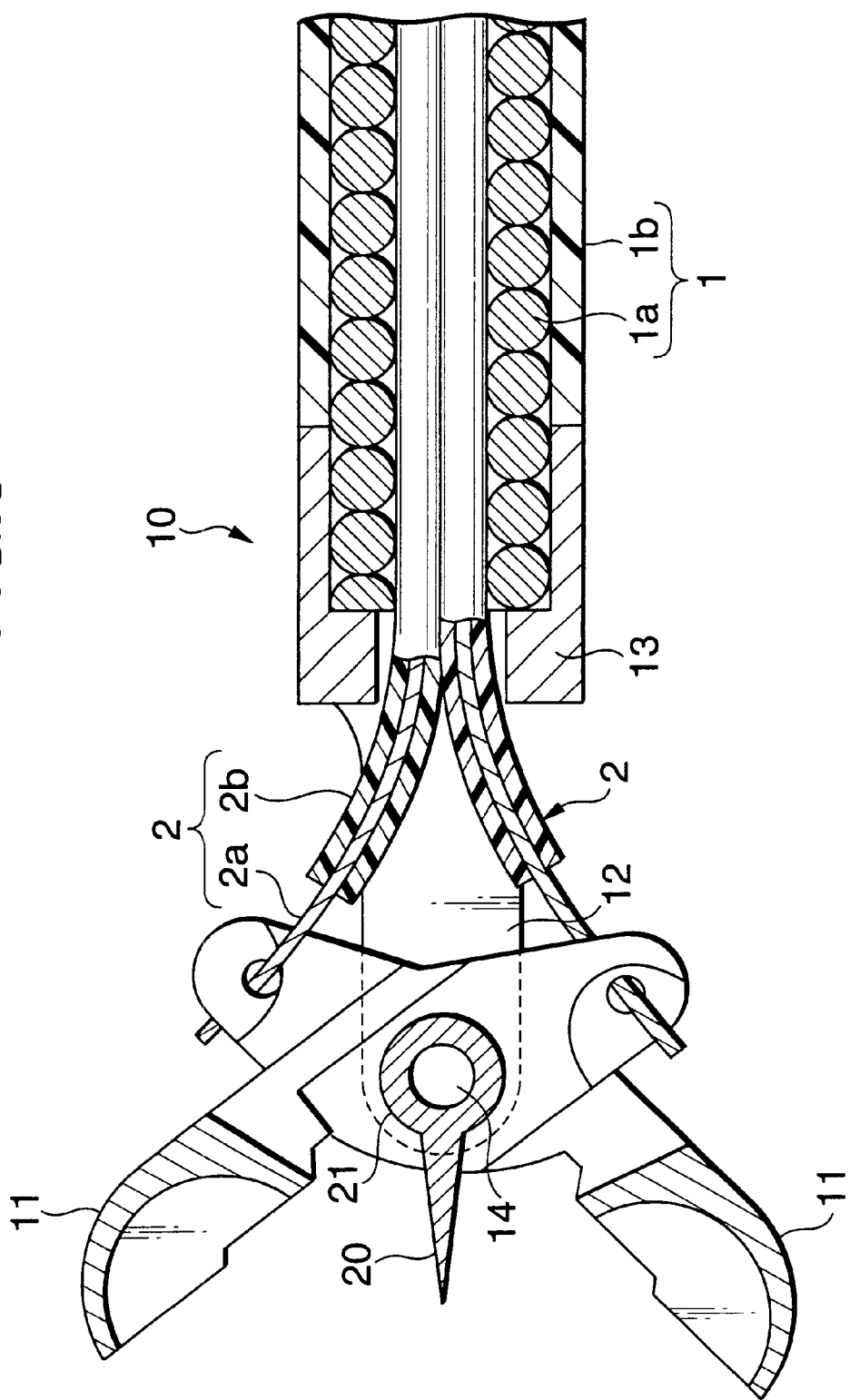
FIG. 6 is a side view showing in section endoscopic biopsy forceps according to a third embodiment of the invention.

FIG. 6 shows a third embodiment of the invention in which it is applied to so-called bipolar radio-frequency biopsy forceps. In this embodiment, two insulated conductor wires are used as manipulating wires 2, each consisting of a lead wire 2a and an insulation coat 2b.

A pair of forceps cups 11 are electrically insulated from each other and connected to different lead wires 2a. Because of this arrangement, high-frequency cautery and coagulation can be performed with the two forceps cups 11 serving as a positive and a negative electrode in the absence of any counter electrode.

In the third embodiment, two needles 20 also extend forward from the distal end of the tip assembly 13 to project into the pair of forceps cups 11. Again, the needles may be adapted to be movable along the peripheries of the forceps cups as in the second embodiment.

It should also be noted that the present invention is by no means limited to the three embodiments described above and various modifications may be made. For instances only one needle 20 may be used or, alternatively, three or more needles may be employed. All that is required is that the needle or needles should be offset from the center of the pair of forceps cups 11.

What is claimed is:

1. Endoscopic biopsy forceps comprising:

a sheath;

a manipulating wire extending through the sheath;

a pair of forceps cups provided at a distal end of the sheath and configured to open and close by advancing and retracting the manipulating wire along a longitudinal axis; and at least one positioning projection commencing at the distal end of the sheath and extending forward to project through the pair of forceps cups, the positioning projection being offset from a center of the pair of forceps cups and configured to pierce a specimen to positionally secure the forceps.

2. The endoscopic biopsy forceps according to claim 1, wherein a plurality of said positioning projections are positioned side by side, each of said positioning projections being offset from the center of said one pair of forceps cups.

3. The endoscopic biopsy forceps according to claim 1, wherein each of said at least one positioning projection is located on an imaginary plane at which said forceps cups abut against each other when said forceps cups are closed completely.

4. The endoscopic biopsy forceps according to claim 1, wherein two of said at least one positioning projections are provided, which are arranged symmetrically to each other with respect to the center of said one pair of forceps cups.

5. The endoscopic biopsy forceps according to claim 1, wherein each of said forceps cups are electrically conductive.

6. The endoscopic biopsy forceps according to claim 5, wherein one of said forceps cups is electrically insulated from the other of said forceps cups.

7. Endoscopic biopsy forceps comprising:

a sheath;

a manipulating wire extending through the sheath;

a pair of forceps cups provided at a distal end of the sheath and configured to open and close by advancing and retracting the manipulating wire along a longitudinal axis; and a plurality of needles that movably extend through the pair of forceps cups, each of the plurality of needles being offset from a center of the pair of forceps cups.

8. The endoscopic biopsy forceps according to claim 7, wherein each of the plurality of needles is positioned on an imaginary plane at which the pair of forceps cups abut against each other when the pair of forceps cups are closed completely.

9. The endoscopic biopsy forceps according to claim 7, wherein each of the pair of forceps cups is electrically conductive.

10. The endoscopic biopsy forceps according to claim 9, wherein one of the forceps cups is electrically insulated from the other of the forceps cups.

11. Endoscopic biopsy forceps comprising:

a sheath;

a manipulating wire extending through the sheath;

a pair of forceps cups provided at a distal end of the sheath and configured to open and close by advancing and retracting the manipulating wire along a longitudinal axis; and a pair of needles that movably extend through the pair of forceps cups, each of the pair of needles being offset from and symmetrically arranged with respect to a center of the pair of forceps cups.

12. The endoscopic biopsy forceps according to claim 11, wherein each of the pair of needles is positioned on an imaginary plane at which the pair of forceps cups abut against each other when the pair of forceps cups are closed completely.

13. The endoscopic biopsy forceps according to claim 11, wherein each of the pair of forceps cups is electrically conductive.

14. The endoscopic biopsy forceps according to claim 13, wherein one of the forceps cups is electrically insulated from the other of the forceps cups.

* * * * *